United States Patent
Hosokawa

(10) Patent No.: US 10,274,373 B2
(45) Date of Patent: Apr. 30, 2019

(54) CONTROL DEVICE, DETECTION DEVICE, AND CONTROL METHOD TO CONTROL AN OPERATION PERFORMED BY THE DETECTION DEVICE ON THE BASIS OF A DETERMINED MOUNTED STATE OF THE DEVICE

(71) Applicant: SONY MOBILE COMMUNICATIONS INC., Tokyo (JP)

(72) Inventor: Satoshi Hosokawa, Tokyo (JP)

(73) Assignee: SONY MOBILE COMMUNICATIONS INC., Tokyo (JP)

( * ) Notice: Subject to any disclaimer, the term of this patent is extended or adjusted under 35 U.S.C. 154(b) by 165 days.

(21) Appl. No.: 15/596,719

(22) Filed: May 16, 2017

(65) Prior Publication Data

US 2017/0343417 A1 Nov. 30, 2017

(30) Foreign Application Priority Data

May 27, 2016 (JP) .................. 2016-106220

(51) Int. Cl.
    *G01J 5/02* (2006.01)
    *A61B 5/0205* (2006.01)
    (Continued)

(52) U.S. Cl.
    CPC ............ *G01J 5/026* (2013.01); *A61B 5/0205* (2013.01); *A61B 5/14551* (2013.01);
    (Continued)

(58) Field of Classification Search
    CPC .............. A61B 5/0205; A61B 5/14551; A61B 5/14552; A61B 5/6886; G01J 1/4204; G01J 5/026
    (Continued)

(56) References Cited

U.S. PATENT DOCUMENTS 5,057,695 A * 10/1991 Hirao ................. A61B 5/14551
    250/575
2013/0131473 A1 5/2013 Gu et al.
(Continued)

FOREIGN PATENT DOCUMENTS

JP 2013-202289 10/2013

OTHER PUBLICATIONS

Extended Search Report dated Oct. 9, 2017 in European Patent Application No. 17169291.6.

*Primary Examiner* — Que Tan Le
(74) *Attorney, Agent, or Firm* — Xsensus LLP

(57) ABSTRACT

There is provided a control device including: a determination unit configured to determine a mounted state of a detection device on the basis of a plurality of detection values, the detection unit including a light source and a plurality of light receiving elements and detecting a pulse wave, the plurality of detection values corresponding to signals output in response to light beams received from the plurality of light receiving elements, respectively, distances between the light source and the respective plurality of light receiving elements being different from each other; and an operation control unit configured to control an operation related to detection of the pulse wave performed by the detection device on the basis of a determination result of the mounted state.

12 Claims, 4 Drawing Sheets

(51) Int. Cl.
   *A61B 5/1455*   (2006.01)
   *G01J 1/42*     (2006.01)
   *G01J 1/44*     (2006.01)
   *A61B 5/00*     (2006.01)

(52) U.S. Cl.
   CPC ........ *A61B 5/14552* (2013.01); *A61B 5/6886* (2013.01); *A61B 5/7207* (2013.01); *G01J 1/4204* (2013.01); *G01J 1/44* (2013.01)

(58) Field of Classification Search
   USPC ........................................................ 250/221
   See application file for complete search history.

(56) References Cited

U.S. PATENT DOCUMENTS

| | | |
|---|---|---|
| 2014/0121471 A1 | 5/2014 | Walker |
| 2014/0275852 A1 | 9/2014 | Hong et al. |
| 2014/0288390 A1 | 9/2014 | Hong et al. |
| 2014/0288391 A1 | 9/2014 | Hong et al. |
| 2014/0288392 A1 | 9/2014 | Hong et al. |
| 2015/0025393 A1 | 1/2015 | Hong et al. |
| 2015/0025394 A1 | 1/2015 | Hong et al. |
| 2015/0088013 A1 | 3/2015 | Nakamura |
| 2015/0201853 A1 | 7/2015 | Hong et al. |
| 2015/0201854 A1 | 7/2015 | Hong et al. |

* cited by examiner

■ LIGHT SOURCE (LED)
□ LIGHT RECEIVING ELEMENT (PD)

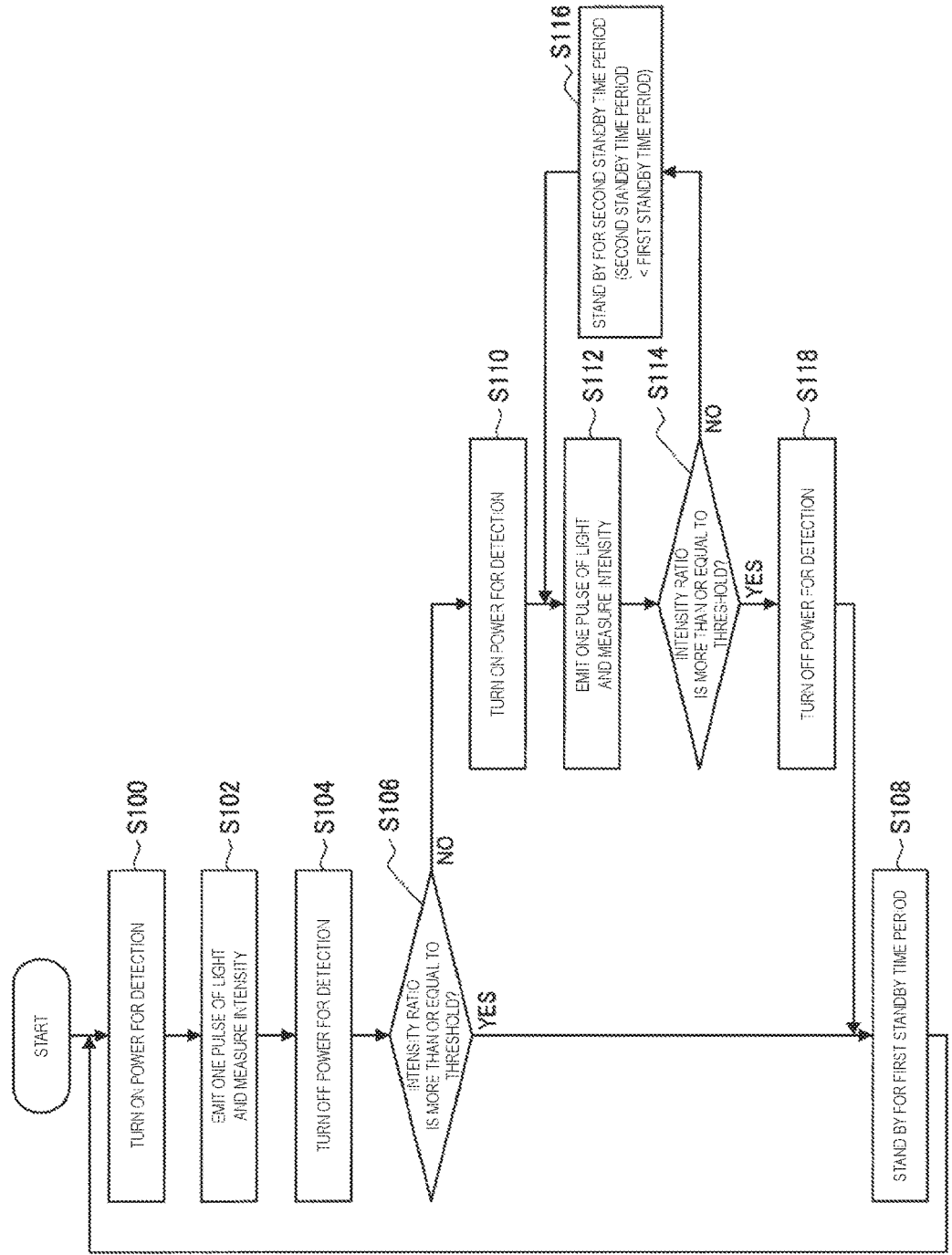

CONTROL DEVICE, DETECTION DEVICE, AND CONTROL METHOD TO CONTROL AN OPERATION PERFORMED BY THE DETECTION DEVICE ON THE BASIS OF A DETERMINED MOUNTED STATE OF THE DEVICE

CROSS REFERENCE TO RELATED APPLICATIONS

This application claims the benefit of Japanese Priority Patent Application JP 2016-106220 filed May 27, 2016, the entire contents of which are incorporated herein by reference.

BACKGROUND

The present disclosure relates to a control device, a detection device, and a control method.

Technology related to a pulsation detection device has been developed, which reduces power consumption in accordance with a determination result of a motion state or the like. The technology related to the pulsation detection device mentioned above includes technology described in JP 2013-202289A, for example.

SUMMARY

As a sensor capable of detecting a signal related to a heartbeat, there is given a pulse wave sensor configured to optically detect a pulse wave using a system called photoplethysmography (hereinafter, may be referred to as "photo detector" (PPG)). The pulse wave is change in a volume of a blood vessel that occurs accompanied by beating of the heart of a living body.

The pulse wave sensor detects a pulse wave of a living body by emitting light from a light source such as a light-emitting diode (LED) on the living body that is a detection target, and obtaining a signal indicating intensity of light reflected from the living body by light receiving elements such as photodiodes (hereinafter, each of which is referred to as "PD"). As described above, in order to detect a pulse wave using PPG, light from a light source is necessary, and hence, in the case where the pulse wave is detected using PPG, the power consumption tends to increase.

For example, a device in which technology described in JP 2013-202289A is used changes the frequency of sensing performed by the pulse wave sensor in accordance with a determination result of a motion state. Accordingly, the power consumption may be reduced by changing the frequency of sensing performed by the pulse wave sensor as the technology described in JP 2013-202289A, for example.

Here, in the case where a user who wears a device including the pulse wave sensor on his/her arm, that is, a human body who is a detection target of the pulse wave sensor, moves, there is a risk that the pulse wave sensor may be influenced by stray light (for example, light other than the light of the detection target such as external light or light reflected on the outer layer of the skin of the human body, the same applies hereinafter), due to the motion of the user, for example. However, even if the frequency of sensing performed by the pulse wave sensor is changed as the technology described in JP 2013-202289A, it is still difficult to reduce the influence of the stray light. Therefore, even if the technology described in JP 2013-202289A is used, it may be difficult to stably detect the pulse wave.

The present disclosure proposes a control device, a detection device, and a control method, which are novel and improved, and which are capable of reducing the power consumption for detecting a pulse wave.

According to an embodiment of the present disclosure, there is provided a control device including: a determination unit configured to determine a mounted state of a detection device on the basis of a plurality of detection values, the detection unit including a light source and a plurality of light receiving elements and detecting a pulse wave, the plurality of detection values corresponding to signals output in response to light beams received from the plurality of light receiving elements, respectively, distances between the light source and the respective plurality of light receiving elements being different from each other; and an operation control unit configured to control an operation related to detection of the pulse wave performed by the detection device on the basis of a determination result of the mounted state.

According to an embodiment of the present disclosure, there is provided a detection device including: a light emission unit including a light source; a light reception unit including a plurality of light receiving elements whose distances from the light source are different from each other; a pulse wave detection unit configured to detect a pulse wave on the basis of a plurality of detection values corresponding to signals output in response to light beams received from the plurality of light receiving elements, respectively; a determination unit configured to determine a mounted state on the basis of the plurality of detection values; and an operation control unit configured to control an operation related to detection of the pulse wave on the basis of a determination result of the mounted state.

According to an embodiment of the present disclosure, there is provided a control method executed by a control device, the control method including: determining a mounted state of a detection device on the basis of a plurality of detection values, the detection unit including a light source and a plurality of light receiving elements and detecting a pulse wave, the plurality of detection values corresponding to signals output in response to light beams received from the plurality of light receiving elements, respectively, distances between the light source and the respective plurality of light receiving elements being different from each other; and controlling an operation related to detection of the pulse wave performed by the detection device on the basis of a determination result of the mounted state.

According to an embodiment of the present disclosure, the power consumption for detecting a pulse wave can be reduced.

Note that the effects described above are not necessarily limitative. With or in the place of the above effects, there may be achieved any one of the effects described in this specification or other effects that may be grasped from this specification.

BRIEF DESCRIPTION OF THE DRAWINGS

FIG. 5 is a flowchart showing an example of processing of a control method according to the present embodiment.

DETAILED DESCRIPTION OF THE EMBODIMENT(S)

Figure 1:
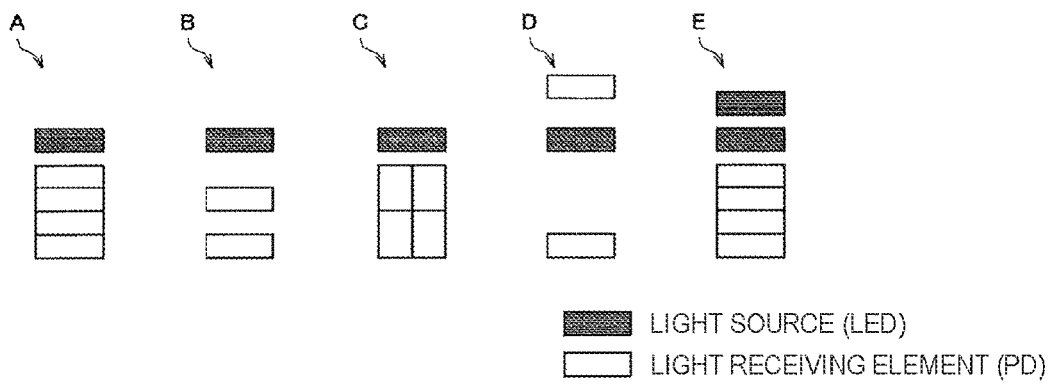
FIG. 1 is an explanatory diagram showing an example of a configuration related to detection of a pulse wave according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Further, hereinafter, the description will be written in the following order.
1. Control method according to the present embodiment
2. Detection device and control device according to the present embodiment
3. Program according to the present embodiment

Control Method According to the Present Embodiment

First, a control method according to the present embodiment will be described. Hereinafter, an example is mainly given of the case where processing of the control method according to the present embodiment is performed by a control device according to the present embodiment.

Note that, as will be described later, the control device according to the present embodiment can also function as a detection device according to the present embodiment. That is, the processing of the control method according to the present embodiment may also be performed by the detection device according to the present embodiment.

An example of the detection device according to the present embodiment that is capable of performing the processing of the control method according to the present embodiment and an example of a configuration of the control device according to the present embodiment will be described later.

[1] Overview of Control Method According to the Present Embodiment

As described above, in order to detect a pulse wave using PPG, light from a light source is necessary, and hence, in the case where the pulse wave is detected using PPG, the power consumption tends to increase.

Here, in a device configured to detect a pulse wave using PPG (device including a pulse wave sensor; hereinafter, referred to as "detection device"), the most part of the power consumption for detecting the pulse wave is the power consumption in the light source. Accordingly, as one method of attempting to reduce the power consumption in the detection device, there is given a "method including determining a mounted state of the detection device on a living body (for example, a human, or an animal other than humans) to be a detection target of a pulse wave, and causing the light source to be selectively emit light depending on the mounted state", for example.

When the above one method is used, in the case where it is determined that the detection device is mounted on the living body, the detection device detects the pulse wave by emitting light from the light source. Further, when the above one method is used, in the case where it is not determined that the detection device is mounted on the living body, the detection device does not emit light from the light source and does not detect the pulse wave.

In the case where it is not determined that the detection device is mounted on the living body, even if the light is emitted from the light source, the probability is high that a signal indicating the intensity of light reflected from the living body to be the detection target cannot be detected, that is, the pulse wave cannot be detected. Accordingly, when the above one method is used, since the light is not emitted from the light source in the case where the probability that the pulse wave cannot be detected is high, the power consumption in the detection device may be reduced.

Here, as a method of determining the mounted state of the detection device, there is given, for example, a method of detecting contact of a living body with a detection device by providing the detection device with a sensor for detecting the contact of the living body with the detection device. Examples of the sensor include the following.

An infrared sensor (a sensor that emits infrared rays and determines contact/non-contact on the basis of the intensity of the reflected light)

A sensor including electrodes placed in a pair on a surface with which the living body comes into contact when mounted (a sensor that utilizes the fact that the living body such as a human body passes electric current and determines contact/non-contact on the basis of a resistance value)

However, in the case where the detection device is provided with the sensor such as the infrared sensor for detecting the contact of the living body with the detection device, there is a risk that the cost of the detection device may increase with the addition of components of the sensor, and that the size of the detection device may increase.

Further, in the case where the detection device is provided with the sensor such as the infrared sensor for detecting the contact of the living body with the detection device, false detection of the mounted state of the detection device may occur, such as false detection due to an external light source such as the sunlight (the case of the above infrared sensor) and false detection due to electrical continuity caused by wetness (the case of the above sensor including electrodes placed in a pair on the contact surface).

Therefore, even if the "method of determining the mounted state of the detection device by providing the detection device with the sensor for detecting the contact of the living body with the detection device" described above is used, the mounted state of the detection device is not necessarily determined. Thus, even if the "method of determining the mounted state of the detection device by providing the detection device with the sensor for detecting the contact of the living body with the detection device" is used, the power consumption in the detection device is not necessarily reduced.

Accordingly, the control device according to the present embodiment determines the mounted state of the detection device by a method different from the above "method of determining the mounted state of the detection device by providing the detection device with the sensor for detecting the contact of the living body with the detection device".

Here, as the mounted states of the detection device determined by the control device according to the present embodiment, there are given a state in which the detection device is mounted and a state in which the detection device is not mounted.

The state in which the detection device according to the present embodiment is mounted represents that the positional relationship between the detection device and the living body to be the detection target of a pulse wave is in a positional relationship capable of detecting the pulse wave using PPG, for example. Example of the positional relationship capable of detecting the pulse wave using PPG include a "positional relationship in which a part for detecting the pulse wave in the detection device with which a light source and light receiving elements are provided is in contact with tissue of the living body to be the detection target of the pulse wave".

Further, the state in which the detection device according to the present embodiment is not mounted represents that the positional relationship between the detection device and the living body to be the detection target of a pulse wave is in a positional relationship incapable of detecting the pulse wave using PPG, for example. Example of the positional relationship incapable of detecting the pulse wave using PPG include a "positional relationship in which a part for detecting the pulse wave in the detection device with which a light source and light receiving elements are provided is not in contact with tissue of the living body to be the detection target of the pulse wave".

The control device according to the present embodiment determines the mounted state of the detection device not by being provided with the sensor such as the infrared sensor for detecting the contact of the living body with the detection device, but by using a configuration related to detection of a pulse wave. The determination of the mounted state using the configuration related to detection of a pulse wave according to the present embodiment will be described later.

The control device according to the present embodiment controls an operation related to detection of a pulse wave performed by the detection device on the basis of a determination result of the mounted state.

Here, the detection device to be controlled (hereinafter, referred to as "detection device to be controlled") the mounted state of which is determined and the operation of which is controlled by the control device according to the present embodiment may be the control device according to the present embodiment, or may be an external device of the control device according to the present embodiment. In the case where the detection device to be controlled is the control device according to the present embodiment, the control device according to the present embodiment that is the detection device to be controlled functions as the detection device according to the present embodiment. Hereinafter, the case where the detection device to be controlled is the control device according to the present embodiment is mainly given as an example.

Further, as the control on the operation related to detection of a pulse wave performed by the detection device according to the present embodiment, there are given, for example, any one of or both of the following (A) "Control on light emission from light source" and the following (B) "Control on power supply to circuit for detecting pulse wave included in detection device". Note that the control on the operation related to detection of a pulse wave according to the present embodiment is not limited to the examples of the following (A) and (B), and the control device according to the present embodiment can control any operation related to detection of a pulse wave.

(A) Control on Light Emission from Light Source

The control device according to the present embodiment changes a light emission frequency of the light source based on whether the determined mounted state is a state in which the detection device is mounted or the determined mounted state is a state in which the detection device is not mounted.

To be more specific, the control device according to the present embodiment controls light emission of the light source such that the light emission frequency of the light source in the case where the determined mounted state is the state in which the detection device is mounted is less than the light emission frequency of the light source in the case where the determined mounted state is the state in which the detection device is not mounted, for example. The light emission frequency of the light source can be changed by controlling a standby time period from the light emission of the light source to the next light emission of the light source, for example.

The control device according to the present embodiment changes the light emission frequency of the light source on the basis of a determination result of the mounted state as described above, and thus, the power consumption in the light source of the detection device in the state in which the detection device is not mounted can be made less than the power consumption in the light source of the detection device in the state in which the detection device is mounted. Accordingly, the control device according to the present embodiment changes the light emission frequency of the light source on the basis of the determination result of the mounted state as described above, and thus, the power consumption for detecting a pulse wave in the state in which the detection device is not mounted can be made less than the power consumption for detecting a pulse wave in the state in which the detection device is mounted.

A specific example of control on light emission from light source on the basis of the determination result of the mounted state will be described later.

(B) Control on Power Supply to Circuit for Detecting Pulse Wave Included in Detection Device The control device according to the present embodiment controls power supply to a circuit for detecting a pulse wave included in the detection device on the basis of the determination result of the mounted state.

The circuit for detecting a pulse wave according to the present embodiment is a circuit used for detecting a pulse wave using PPG, for example. The circuit for detecting a pulse wave according to the present embodiment includes, for example, a circuit for acquiring a detection value (to be described later) used for detecting a pulse wave (hereinafter, referred to as "circuit for acquiring a detection value") and a circuit for detecting a pulse wave on the basis of the detection value (to be described later) (hereinafter, referred to as "pulse wave detection circuit"). Specific example of the circuit for detecting a pulse wave according to the present embodiment will be described later.

To be more specific, the control device according to the present embodiment performs control such that, in the case where the determined mounted state is the state in which the detection device is not mounted, the circuit for detecting a pulse wave is not supplied with power, for example. That is, in the case where the determined mounted state is the state in which the detection device is not mounted, operation of the circuit for detecting a pulse wave included in the detection device is stopped, and no power is consumed in the circuit for detecting a pulse wave.

Further, in the case where the determined mounted state is the state in which the detection device is mounted, the control device according to the present embodiment performs control such that the circuit for detecting a pulse wave is supplied with power.

The control device according to the present embodiment controls power supply to the circuit for detecting a pulse wave by controlling a switching circuit (to be described later) included in the detection device, for example.

The control device according to the present embodiment controls power supply to the circuit for detecting a pulse wave included in the detection device on the basis of a determination result of the mounted state as described above, and thus, the power consumption for detecting a pulse wave in the state in which the detection device is not mounted can be made less than the power consumption for detecting a pulse wave in the state in which the detection device is mounted.

As shown in the above (A) and (B), for example, the control device according to the present embodiment controls the operation of the detection device on the basis of the determination result of the mounted state of the detection device.

Here, the operation of the detection device is controlled on the basis of the determination result of the mounted state, and thus, the power consumption for detecting a pulse wave in the state in which the detection device is not mounted can be made less than the power consumption for detecting a pulse wave in the state in which the detection device is mounted.

Accordingly, the control device according to the present embodiment can reduce the power consumption for detecting the pulse wave by performing the processing of the control method according to the present embodiment.

[2] Processing of Control Method According to the Present Embodiment

Next, processing of a control method according to the present embodiment will be described.

The control device according to the present embodiment performs, as the processing of the control method according to the present embodiment, the following processing (1) (Determination processing) and the following processing (2) (Control processing), for example.

(1) Determination Processing

As described above, the control device according to the present embodiment determines the mounted state of the detection device by using a configuration related to detection of a pulse wave that the detection device has.

As the configuration related to detection of a pulse wave according to the present embodiment, there are given a light source and a plurality of light receiving elements whose distances from the light source are different from each other.

Examples of the light source according to the present embodiment include an LED and a laser light source. The light source is not limited to the examples shown above, and may be any element (or any circuit) which is capable of emitting light. Hereinafter, an example is given in the case where the light source according to the present embodiment is an LED.

As the light emitted by the light source, there are given light beams having various wavelengths, such as green, red, and near infrared light beams.

Further, the configuration related to detection of a pulse wave may include a plurality of light sources. The colors of light beams (wavelengths of light beams) emitted by the plurality of light sources may be the same or different from each other.

Examples of the light receiving elements according to the present embodiment include a PD, a phototransistor, and a charge coupled device (CCD) Note that the light receiving elements are not limited to the examples shown above, and may be any element (or any circuit) which is capable of outputting a signal corresponding to intensity of incident light. Further, the plurality of light receiving elements have the same characteristics, for example. Hereinafter, an example is given in the case where the light receiving elements according to the present embodiment are PD's.

FIG. 1 is an explanatory diagram showing an example of a configuration related to detection of a pulse wave according to the present embodiment. In FIG. 1, A to E each represent an example of a placement relationship between a light source and a plurality of light receiving elements. In FIG. 1, an LED is shown as an example of the light source, and a PD is shown as an example of each of the light receiving elements.

As shown in FIG. 1, the configuration related to detection of a pulse wave according to the present embodiment includes a plurality of light receiving elements, and includes two or more combinations of a light source and the light receiving elements, in which the distances between the light source and the respective light receiving elements are different from each other.

A of FIG. 1 represents an example in which four light receiving elements are included and a placement relationship in which the distances between the light source and the respective light receiving elements are different from each other. B of FIG. 1 represents an example in which two light receiving elements are included and a placement relationship in which the distances between the light source and the respective light receiving elements are different from each other.

Further, as long as the configuration related to detection of a pulse wave satisfies the condition that two or more combinations of a light source and light receiving elements in which the distances between the light source and the respective light receiving elements are different from each other, the light source and the plurality of light receiving elements can have various placement relationships, as shown in C and D of FIG. 1.

For example, as shown in C of FIG. 1, there may be two or more light receiving elements whose distances from the light source are the same.

Further, as shown in D of FIG. 1, the configuration related to detection of a pulse wave may have the light receiving elements provided in different directions when seen from the light source. Note that, although D of FIG. 1 shows an example in which two light receiving elements are placed so as to sandwich the light source, any placement relationship may be taken that the directions in which the light receiving elements are placed are different when seen from the light source, for example, the plurality of light receiving elements may be placed in an "L" shape when seen from the light source.

Moreover, as shown in E of FIG. 1, the configuration related to detection of a pulse wave may include a plurality of light sources.

As the configuration related to detection of a pulse wave according to the present embodiment, there are given, as shown in FIG. 1, a light source and a plurality of light receiving elements whose distances from the light source are different from each other. Note that it is needless to say that the example of the configuration related to detection of a pulse wave according to the present embodiment is not limited to the example shown in FIG. 1.

Next, a principle of determination of a mounted state using the configuration related to the detection of a pulse wave according to the present embodiment will be described.

Figure 2:
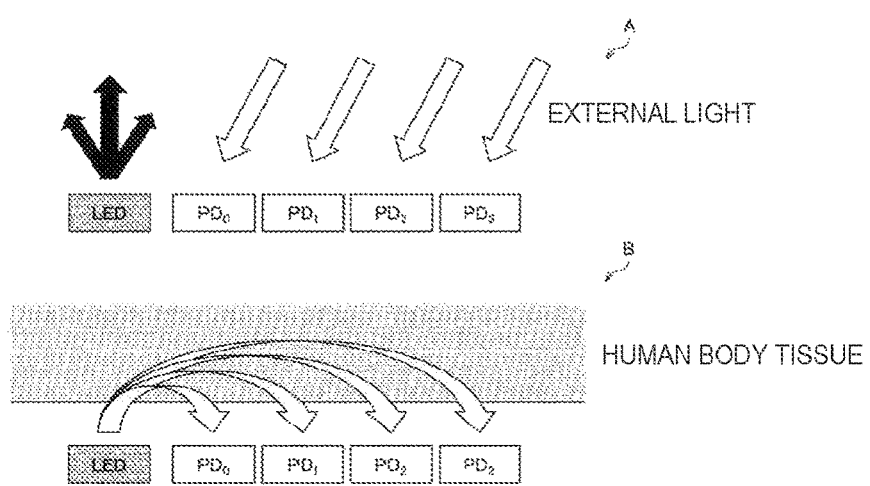
FIG. 2 is a block diagram illustrating a principle of determination of a mounted state using the configuration related to the detection of a pulse wave according to the present embodiment.

FIG. 2 is a block diagram illustrating a principle of determination of a mounted state using the configuration related to the detection of a pulse wave according to the present embodiment. FIG. 2 shows a change in a light path between the case where the detection device is not mounted on a human body (an example of a living body that is a detection target of a pulse wave, the same applies hereinafter) and the case where the detection device is mounted on the human body. A of FIG. 2 shows the case where the detection device is not mounted on the human body (that is, the positional relationship between the detection device and the human body is not in the positional relationship capable of detecting the pulse wave using PPG). Further, B of FIG. 2 shows the case where the detection device is mounted on the human body (that is, the positional relationship between the detection device and the human body is in the positional relationship capable of detecting the pulse wave using PPG).

In FIG. 2, an LED is shown as a light source, and a PD is shown as a light receiving element. FIG. 2 shows four PD's whose distances from the LED are different from each other.

In the case where the detection device is not mounted on the human body, as shown in A of FIG. 2, the light emitted from the LED is only emitted in space and does not enter the PD's. Accordingly, the component of light received by the PD's in the case where the detection device is not mounted on the human body is only external light emitted by a light source other than the LED, which is present in an environment.

In this case, the distance between the plurality of PD's included in the detection device can be considered to be sufficiently smaller than the distance between each of the plurality of PD's included in the detection device and the light source present in the environment. Accordingly, it can be considered that difference in relative directions between the light source present in the environment and the respective PD's and difference attributed to distance difference do not occur in signals (each indicating intensity of light) that are output in response to light reception from the respective PD's included in the detection device.

Therefore, in the case where the detection device is not mounted on the human body, the values indicated by the signals output in response to light reception from the respective PD's included in the detection device are approximately the same.

Here, the value indicated by the signal output in response to light reception from the PD (an example of the light receiving element) represents a value indicating intensity of light that enters the PD. Further, the value indicated by the signal output in response to light reception from the PD may be a value indicated by a signal which is obtained by amplifying the signal output in response to light reception from the PD by an amplification circuit. Hereinafter, the value indicated by the signal output in response to light reception from the light receiving element or the value indicated by the signal which is obtained by amplifying the relevant signal is represented by "detection value corresponding to a signal output in response to light reception from a light receiving elements" or simply "detection value".

In other words, in the case where the detection device is not mounted on the human body, the ratio of a detection value corresponding to intensity of light that enters a PD whose distance from the LED is small to a detection value corresponding to intensity of light that enters a PD whose distance from the LED is larger is "1" (or a value that can be regarded as "1").

On the other hand, in the case where the detection device is mounted on the human body, as shown in B of FIG. 2, external light emitted by a light source present in the environment is disturbed by human body tissue and does not reach the PD.

Further, in the case where the detection device is mounted on the human body, the light emitted from the LED dispersedly propagates inside the human body tissue and enters the PD. In this case, since some of the light is absorbed in the human body tissue in the process of dispersion, the light beams that are received at the respective PD's decrease in accordance with the distances from the LED.

In the configuration related to detection of a pulse wave shown in FIG. 2, the distances between the LED that is the light source and the respective PD's that are the light receiving elements are different from each other depending on the PD's. Accordingly, in the case where the detection device is mounted on the human body, in the configuration related to detection of a pulse wave shown in FIG. 2, the intensity of light that enters a PD decreases as the distance between the LED and a PD increases. That is, in the case where the detection device is mounted on the human body, in the configuration related to detection of a pulse wave shown in FIG. 2, the ratio of a detection value corresponding to intensity of light that enters a PD whose distance from the LED is small to a detection value corresponding to intensity of light that enters a PD whose distance from the LED is larger is a value less than "1" (a small value that cannot be regarded as "1").

As shown with reference to FIG. 2, the control device according to the present embodiment determines the mounted state of the detection device by using the fact that "the plurality of detection values corresponding to signals output in response to light beams received from the respective light receiving elements are different between the case where the detection device is mounted on the living body and the case where detection device is not mounted on the living body".

That is, the control device according to the present embodiment determines the mounted state of the detection device on the basis of the plurality of detection values corresponding to signals output in response to light beams received from the respective light receiving elements whose distances from the light source are different from each other.

(2) Control Processing

The control device according to the present embodiment controls an operation related to detection of a pulse wave performed by the detection device on the basis of a determination result of a mounted state in the above processing (1)

(Determination Processing).

The control device according to the present embodiment performs, as the control on the operation related to detection of a pulse wave, one of or both of the above (A) "Control on light emission from light source" and the above (B) "Control on power supply to circuit for detecting pulse wave included in detection device", for example.

As the processing of the control method according to the present embodiment, the control device according to the present embodiment performs the above processing (1) (Determination processing) and the above processing (2) (Control processing), for example.

In the above processing (2) (Control processing), the control device according to the present embodiment controls the operation related to detection of a pulse wave performed by the detection device on the basis of a determination result of a mounted state in the above processing (1) (Determination processing).

Here, the operation of the detection device is controlled on the basis of the determination result of a mounted state in the above processing (1) (Determination processing), and thus, the power consumption for detecting a pulse wave in the state in which the detection device is not mounted can be made less than the power consumption for detecting a pulse wave in the state in which the detection device is mounted.

Accordingly, the control device according to the present embodiment can reduce the power consumption for detecting the pulse wave by performing the processing of the control method according to the present embodiment.

Further, in the above processing (2) (Control processing), the control device according to the present embodiment performs one of or both of the control on light emission from the light source and the control on power supply to the circuit for detecting a pulse wave, on the basis of the determination result of a mounted state, for example. Accordingly, in the detection device, automatic switching of the light emission frequency is achieved corresponding to the determination result of a mounted state by the control device according to the present embodiment. Therefore, with the processing of the control method according to the present embodiment being performed, the convenience of the user of the detection device can be enhanced.

Further, in the above processing (1) (Determination processing), the control device according to the present embodiment determines the mounted state of the detection device using the configuration related to detection of a pulse wave that the detection device has. Therefore, in the case where the control method according to the present embodiment is used, it is not necessary to provide the detection device with a sensor for detecting contact of a living body with the detection device, such as an infrared sensor.

Consequently, in the case where the control method according to the present embodiment is used, the cost of the detection device may be reduced as compared to the case where the detection device is provided with a sensor for detecting contact of a living body with the detection device, such as an infrared sensor. Moreover, in the case where the control method according to the present embodiment is used, the size of the detection device can be reduced as compared to the case where the detection device is provided with a sensor for detecting contact of a living body with the detection device, such as an infrared sensor.

In addition, since the control device according to the present embodiment determines the mounted state of the detection device using the configuration related to detection of a pulse wave that the detection device has, false detection of the mounted state caused by a foreign substance such as external light or water does not occur.

Therefore, the control device according to the present embodiment can determine more accurately the mounted state than the case of using the "method of determining the mounted state of the detection device by providing the detection device with the sensor for detecting the contact of the living body with the detection device". Moreover, since the mounted state can be determined more accurately, the control device according to the present embodiment can reduce the power consumption for detecting the pulse wave more than the case of using the "method of determining the mounted state of the detection device by providing the detection device with the sensor for detecting the contact of the living body with the detection device", and the convenience of the user of the detection device can be enhanced.

Note that "the above processing (1) (Determination processing) and the above processing (2) (Control processing)" are obtained by dividing the processing of the control method according to the present embodiment as a matter of convenience. Accordingly, in the processing of the control method according to the present embodiment, "the above processing (1) (Determination processing) and the above processing (2) (Control processing)" can be regarded as one piece of processing, for example. Alternatively, in the processing of the control method according to the present embodiment, "the above processing (1) (Determination processing) and the above processing (2) (Control processing)" can also be regarded as two or more pieces of processing (the processing may be divided in any way), for example.

Detection Device and Control Device According to the Present Embodiment

Next, an example of a configuration of a device capable of performing the processing of the control method according to the present embodiment will be described. Hereinafter, as an example of the configuration of a device capable of performing the processing of the control method according to the present embodiment, a configuration of the detection device according to the present embodiment configured to detect a pulse wave using PPG will be mainly described.

[I] Detection Device According to the Present Embodiment

Figure 3:
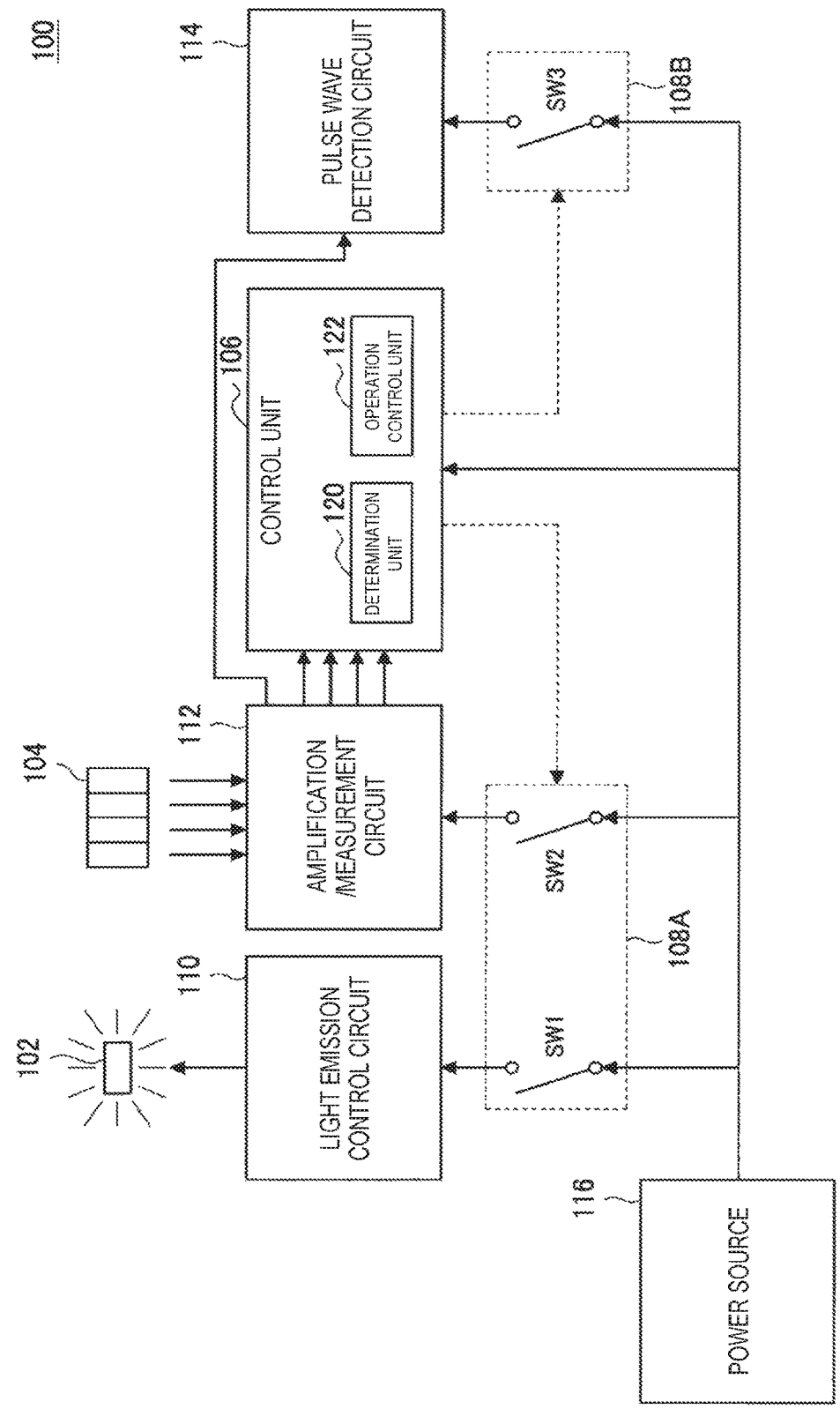
FIG. 3 is a block diagram illustrating an example of a configuration of a detection device according to the present embodiment.

FIG. 3 is a block diagram illustrating an example of a configuration of a detection device 100 according to the present embodiment. The detection device 100 includes, for example, a light emission unit 102, a light reception unit 104, a control unit 106, switch units 108A and 108B, a light emission control circuit 110, an amplification/measurement circuit 112, a pulse wave detection circuit 114, and a power source 116.

Further, the detection device 100 may include, for example, one or more of a read only memory (ROM) (not shown), a random access memory (RAM) (not shown), a storage (not shown), a communication unit (not shown), a manipulation unit (not shown) that can be manipulated by a user of the detection device 100, and a display (not shown) that displays various screens on a display screen. The detection device 100 connects the above-mentioned structural elements via a bus as a transmission path of data, for example. Moreover, the detection device 100 is driven by power supplied by the power source 116 included in the detection device 100 or power supplied by a connected external power source, for example.

The ROM (not shown) stores data for performing control, such as programs and arithmetic parameters used by the control unit 106. The RAM (not shown) temporarily stores programs and the like executed by the control unit 106.

The storage (not shown) is storage means included in the detection device 100, and stores various types of data such as various applications. Examples of the storage (not shown) include a magnetic recording medium such as a hard disk, and a non-volatile memory such as a flash memory. Further, the storage (not shown) may be attachable to and detachable from the detection device 100.

The communication unit (not shown) is communication means included in the detection device 100, and communicates through a network (or directly) with an external device by wire or radio. Examples of communication devices included in the communication unit (not shown) include a communication antenna and a radio frequency (RF) circuit (radio communication), an IEEE802.15.1 port and a transmission/reception circuit (radio communication), an IEEE802.11 port and a transmission/reception circuit (radio communication), and a local area network (LAN) terminal and a transmission/reception circuit (wired communication).

The manipulation unit (not shown) includes a manipulation input device, for example. Examples of the manipulation input device include a button, a direction key, a rotary selector such as a jog dial, and a combination thereof.

Further, the display (not shown) includes a display device, for example. Examples of the display device include a liquid crystal display, and an organic electro-luminescence display (also called organic light emitting diode (OLED) display). In addition, the display device may also be a device capable of performing display and accepting manipulation, such as a touch panel.

The light emission unit 102 includes one or more light sources. Example of the light source includes an LED.

The light reception unit 104 includes a plurality of light receiving elements whose distances from the light source are different from each other. Example of the light receiving element includes a photodiode.

The control unit 106 controls the entire detection device 100.

Further, the control unit 106 includes a determination unit 120 and an operation control unit 122, for example, and plays a role of leadingly performing the processing of the control method according to the present embodiment.

The control unit 106 includes, for example, one or more processors including arithmetic circuits such as a micro processing unit (MPU), a central processing unit (CPU), a digital signal processor (DSP), and various types of processing circuits. In the processor, any processing is performed by executing software, for example. Note that one of or both of the determination unit 120 and the operation control unit 122 to be described later may be achieved by a dedicated (or versatile) circuit that can achieve processing of each unit.

The determination unit 120 plays a role of performing the above processing (1) (Determination processing), and determines the mounted state of the detection device. FIG. 3 shows an example in which the determination unit 120 determines the mounted state of the detection device on the basis of a detection value transmitted by the amplification/measurement circuit 112.

For example, the determination unit 120 calculates a determination value for determining the mounted state on the basis of a plurality of detection values corresponding to two or more light receiving elements, respectively, the distances between the light source and the respective light receiving elements being different from each other.

As an example, the determination unit 120 selects, from the plurality of light receiving elements, any two light receiving elements whose distances from the light source are different from each other. Then, the determination unit 120 calculates, as shown in the following Equation 1, for example, a ratio between two detection values corresponding to the respective selected two light receiving elements, and sets the calculated ratio as the determination value.

Ratio between detection values=(the detection value corresponding to the light receiving element whose distance from the light source is larger)/(the detection value corresponding to the light receiving element whose distance from the light source is smaller)  (Equation 1)

As another example, the determination unit 120 selects, for example, from the plurality of light receiving elements, any three or more light receiving elements whose distances from the light source are different from each other. Then, the determination unit 120 calculates a gradient of three or more detection values corresponding to the respective selected three or more light receiving elements, for example, and sets the calculated gradient as the determination value. The determination unit 120 arranges the detection values in the order of distance from the light source and calculates the gradient of the detection values, for example.

Then, the determination unit 120 determines the mounted state by comparing the calculated determination value to a predetermined threshold.

When the ratio is given as an example of the determination value, as described above, in the case where the detection device is not mounted on the human body, the ratio between the detection values is "1" (or a value that can be regarded as "1"). Further, as described above, in the case where the detection device is mounted on the human body, the ratio between the detection values is a value less than "1" (a small value that cannot be regarded as "1"). Moreover, when the gradient of the detection values is given as an example of the determination value, in the case where the detection device is not mounted on the human body, the gradient of the detection values is "a value near 0".

Figure 4:
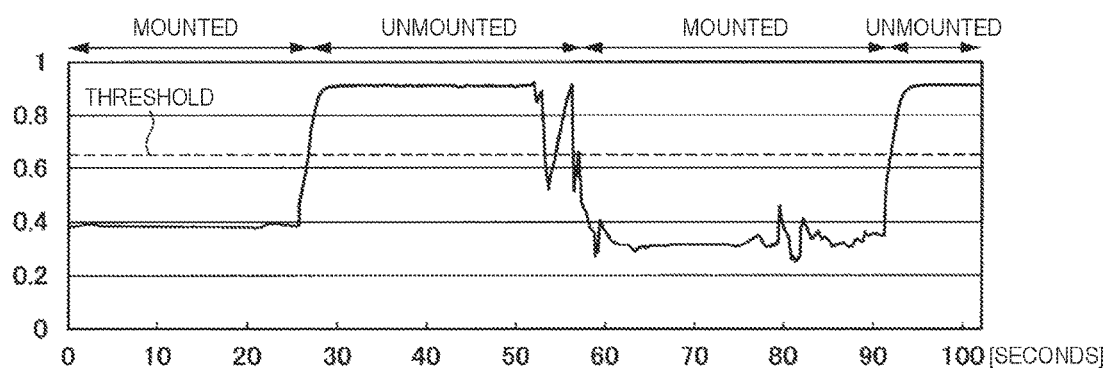
FIG. 4 is an explanatory diagram illustrating an example of a predetermined threshold according to the present embodiment.

FIG. 4 is an explanatory diagram illustrating an example of a predetermined threshold according to the present embodiment. FIG. 4 shows an example of a graph representing, with regard to a detection device including one LED (an example of a light source) and two PD's (examples of light receiving elements) whose distances from the LED are different from each other, measurement of an intensity ratio of signals measured at the two PD's (ratio between detection values) while the mounted state is being changed between mounted and unmounted. In FIG. 4, a period represented by "mounted" represents a period in which the detection device is mounted, and a period represented by "unmounted" represents a period in which the detection device is not mounted.

As shown in FIG. 4, the ratio undergoes a large change in accordance with mounting and unmounting of the detection device, and, in the example shown in FIG. 4, it can be understood that the mounting and unmounting of the detection device can be accurately determined if the threshold is set to a value of approximately 0.6 to 0.7.

The determination unit 120 determines the mounted state by performing threshold processing by setting as the threshold a value that can be used for accurately determining the mounting and unmounting of the detection device 100, like the threshold set in the example shown in FIG. 4, for example.

Note that it is needless to say that the example of the predetermined threshold according to the present embodiment is not limited to the value of approximately 0.6 to 0.7. Further, the predetermined threshold according to the present embodiment may be a fixed value, or may be a variable value that can be changed in accordance with manipulation performed by a user or the like of the detection device 100.

The operation control unit 122 plays a role of performing the above processing (2) (Control processing), and controls the operation related to detection of a pulse wave performed by the detection device on the basis of a determination result of a mounted state in the determination unit 120.

For example, the operation control unit 122 controls light emission of the light source included in the detection device 100 on the basis of the determination result of a mounted state.

To be specific, the operation control unit 122 changes a light emission frequency of the light source based on whether the determined mounted state is a state in which the detection device 100 is mounted or the determined mounted state is a state in which the detection device 100 is not mounted. Specific examples of the change in the light emission frequency of the light source on the basis of the determined mounted state will be described later.

Further, the operation control unit 122 controls power supply to a circuit for detecting a pulse wave included in the detection device 100 on the basis of the determination result of a mounted state, for example. Here, in the exemplary configuration shown in FIG. 3, the light emission control circuit 110, the amplification/measurement circuit 112, and the pulse wave detection circuit 114 each correspond to the circuit for detecting a pulse wave.

To be specific, the operation control unit 122 impresses a control signal that controls a switching circuit (to be described later) on each of switching circuits included in the switch units 108A and 108B, and controls an ON state and an OFF state of the switching circuits to thereby control power supply to each of the circuits for detecting a pulse wave.

For example, in the case where one switching circuit is in the OFF state, power supply to the circuit for detecting a pulse wave corresponding to the switching circuit which is in the OFF state is interrupted. In this case, the circuit for detecting a pulse wave corresponding to the switching circuit which is in the OFF state does not consume power. Further, for example, in the case where one switching circuit is in the ON state, power is supplied to the circuit for detecting a pulse wave corresponding to the switching circuit which is in the ON state.

The control unit 106 includes the determination unit 120 and the operation control unit 122, for example, and thus leadingly performs the processing of the control method according to the present embodiment (for example, the above processing (1) (Determination processing) and the above processing (2) (Control processing)).

The switch units 108A and 108B include switching circuits SW1, SW2, and SW3 corresponding to the following circuits for detecting a pulse wave, respectively.

Switching circuit SW1: a switching circuit corresponding to the light emission control circuit 110 (an example of the circuit for detecting a pulse wave)

Switching circuit SW2: a switching circuit corresponding to the amplification/measurement circuit 112 (an example of the circuit for detecting a pulse wave)

Switching circuit SW3: a switching circuit corresponding to the pulse wave detection circuit 114 (an example of the circuit for detecting a pulse wave)

The switching circuits SW1, SW2, and SW3 each include a switching transistor, for example, and each become the ON state (conduction state) or the OFF state (non-conduction state) in accordance with a signal level (voltage level) of the impressed control signal.

Examples of the switching transistor include a bipolar transistor, and a field-effect transistor (FET) such as a thin film transistor (TFT) and a metal-oxide-semiconductor field effect transistor (MOSFET). Note that each of the switching circuits SW1, SW2, and SW3 is not limited to the switching transistor, and may be any element (or circuit) capable of performing switching between the ON state and the OFF state.

The light emission control circuit 110 is a circuit for detecting a pulse wave included in the detection device 100, and corresponds to an example of the circuit for acquiring a detection value. Example of the light emission control circuit 110 includes a pulse emitting circuit using pulse width modulation (PWM) control. Note that, in the case where other structural elements included in the detection device 100, such as the control unit 106, includes a circuit having a function similar to the light emission control circuit 110, the detection device according to the present embodiment does not necessarily include the light emission control circuit 110.

The amplification/measurement circuit 112 is a circuit for detecting a pulse wave included in the detection device 100, for example, and corresponds to another example of the circuit for acquiring a detection value. The amplification/measurement circuit 112 includes an amplification circuit and a measurement circuit, for example. The amplification circuit and the measurement circuit included in the amplification/measurement circuit 112 each have ability to process signals output from the respective plurality of light receiving elements.

Example of the amplification circuit included in the amplification/measurement circuit 112 includes any amplification circuit capable of amplifying signals output from light receiving elements, such as an operational amplifier. Note that the amplification/measurement circuit 112 does not necessarily include the amplification circuit.

Further, example of the measurement circuit included in the amplification/measurement circuit 112 includes a circuit for integrating and measuring the intensity of signals output from the light receiving elements or signals amplified by the amplification circuit. In the exemplary configuration shown in FIG. 3, the measurement circuit included in the amplification/measurement circuit 112 can obtain detection values corresponding to the respective plurality of light receiving elements. Note that, for example, in the case where other structural elements included in the detection device 100, such as the control unit 106, includes a circuit having a function similar to the light emission control circuit 110, the detection device according to the present embodiment does not necessarily include the light emission control circuit 110.

The pulse wave detection circuit 114 is a circuit for detecting a pulse wave on the basis of a plurality of detection values. The pulse wave detection circuit 114 functions as, in the detection device 100, a pulse wave detection unit configured to detect a pulse wave on the basis of the plurality of detection values.

To the pulse wave detection circuit 114, a plurality of signals which indicate detection values corresponding to the respective plurality of light receiving elements or one signal corresponding to a plurality of detection values are/is input, for example, and the pulse wave detection circuit 114 processes the input signal(s). Examples of the one signal corresponding to a plurality of detection values include a signal in which the plurality of detection values are added up, and a signal indicating an average of the plurality of detection values.

The pulse wave detection circuit 114 includes a circuit of any configuration, which is capable of achieving a function of calculating a pulse frequency every predetermined period, for example, per one minute, on the basis of the change in light intensity values indicated by the plurality of detection values, for example.

Note that, in the case where other structural elements included in the detection device 100, such as the control unit 106, includes a circuit having a function similar to the pulse wave detection circuit 114, the detection device according to the present embodiment does not necessarily include the pulse wave detection circuit 114.

The power source 116 is an internal power source included in the detection device 100. Example of the power source 116 includes a battery including a secondary battery. Note that, in the case where the detection device according to the present embodiment is operated using an external power source, the detection device according to the present embodiment does not necessarily include the power source 116.

The detection device 100 performs the processing of the control method according to the present embodiment (for example, the above processing (1) (Determination processing) and the above processing (2) (Control processing)) with the configuration shown in FIG. 3, for example.

Accordingly, the detection device 100 can reduce the power consumption for detecting a pulse wave with the configuration shown in FIG. 3, for example.

Further, the detection device 100 can achieve, with the configuration shown in FIG. 3, for example, the effects that are achieved by performing the processing of the control method according to the present embodiment.

Note that the configuration of the detection device according to the present embodiment is not limited to the configuration shown in FIG. 3.

For example, the detection device according to the present embodiment may include one of or both of the determination unit 120 and the operation control unit 122 shown in FIG. 3 separately from the control unit 106 (for example, may achieve one of or both of the determination unit 120 and the operation control unit 122 in another processing circuit).

Further, as described above, the above processing (1) (Determination processing) and the above processing (2) (Control processing) are obtained by dividing the processing of the control method according to the present embodiment as a matter of convenience. Accordingly, the configuration for achieving the processing of the control method according to the present embodiment is not limited to the determination unit 120 and the operation control unit 122 shown in FIG. 3, and can have a configuration corresponding to the way of dividing the processing of the control method according to the present embodiment.

Further, the detection device according to the present embodiment may have a configuration corresponding to an example of application of the detection device to be described later, for example.

FIG. 5 is a flowchart showing an example of processing of a control method according to the present embodiment. FIG. 5 shows an example of the processing performed by the detection device 100 shown in FIG. 3.

The detection device 100 turns on the power for detecting a pulse wave (S100). In Step S100, for example, the control unit 106 transmits, to the switching circuits SW1, SW2, and SW3 included in the switch units 108A and 108B, a control signal that causes each of the switching circuits SW1, SW2, and SW3 to be in the ON state, and then the power for detecting a pulse wave is turned on. Further, in Step S100, the light emission control circuit 110 (an example of the circuit for detecting a pulse wave, the same applies hereinafter), the amplification/measurement circuit 112 (an example of the circuit for detecting a pulse wave, the same applies hereinafter), and the pulse wave detection circuit 114 (an example of the circuit for detecting a pulse wave, the same applies hereinafter) are supplied with power.

Note that, the processing of Step S100 is processing performed for determining the mounted state of the detection device 100 before the detection of a pulse wave. Therefore, in Step S100, the control unit 106 does not necessarily transmit, to the switching circuit SW3 included in the switch 108B, the control signal that causes the switching circuit SW3 to be in the ON state, and does not necessarily cause the pulse wave detection circuit 114 to be supplied with power.

The detection device 100 causes a light emitting device to emit one pulse of light and measures intensity of the received light on the basis of signals output from light receiving elements (S102). In Step S102, the light emitting device emits one pulse of light by the control performed by the light emission control circuit 110, and detection values corresponding to the respective light receiving elements are obtained by the amplification/measurement circuit 112.

The detection device 100 turns off the power for detecting a pulse wave (S104). In Step S104, for example, the control unit 106 transmits, to the switching circuits SW1, SW2, and SW3 included in the switch units 108A and 108B, a control signal that causes each of the switching circuits SW1, SW2, and SW3 to be in the OFF state, and then the power for detecting a pulse wave is turned off. Further, in Step S104, the power supply is interrupted to the light emission control circuit 110, the amplification/measurement circuit 112, and the pulse wave detection circuit 114.

The detection device 100 determines whether or not an intensity ratio (an example of the determination value, the same applies hereinafter) based on the detection values obtained in Step S102 is more than or equal to a set threshold (S106). Further, in Step S106, the detection device 100 may also determine whether or not the intensity ratio is more than the set threshold. The processing of Step S106 is performed by the control unit 106, for example. Moreover, the processing of Step S106 corresponds to the processing of determining the mounted state of the detection device 100.

Here, in Step S106, in the case where the intensity ratio is determined to be more than or equal to the set threshold, the case corresponds to the state in which the detection device 100 is not mounted. Further, in Step S106, in the case where the intensity ratio is not determined to be more than or equal to the set threshold, the case corresponds to the state in which the detection device 100 is mounted.

In Step S106, in the case where the intensity ratio is determined to be more than or equal to the set threshold, the detection device 100 stands by for a set first standby time period (S108). Then, the detection device 100 repeats the processing from Step S100.

Here, the first standby time period according to the present embodiment is, for example, several seconds to several minutes. The first standby time period may be a fixed period that has been set in advance, or may be a variable period that can be changed in accordance with manipulation performed by a user or the like of the detection device 100.

Further, in Step S106, in the case where the intensity ratio is not determined to be more than or equal to the set threshold, the detection device 100 turns on the power for detecting a pulse wave in the same manner as in Step S100 (S110)

Note that, the processing of Step S110 is processing performed for detecting the pulse wave. Therefore, in Step S110, the control unit 106 transmits, to the switching circuits SW1, SW2, and SW3 included in the switch units 108A and 108B, a control signal that causes each of the switching circuits SW1, SW2, and SW3 to be in the ON state, and then the circuits for detecting a pulse wave are each supplied with power.

When the processing of Step S110 is performed, the detection device 100 measures, in the same manner as in Step S102, intensity of the received light on the basis of signals output from light receiving elements (S112)

In the same manner as in Step S106, the detection device 100 determines whether or not the intensity ratio based on the detection values obtained in Step S112 is more than or equal to a set threshold (S114). Further, in Step S114, the detection device 100 may also determine whether or not the intensity ratio is more than the set threshold. The processing of Step S114 corresponds to the processing of determining the mounted state of the detection device 100.

Here, the threshold in Step S114 and the threshold in Step S106 may be the same value. Note that the threshold in Step S114 may be a value larger than the threshold in Step S106. By setting the value of the threshold in Step S114 larger than the value of the threshold in Step S106, the determination on the mounted state of the detection device 100 can be made more stable.

In Step S114, in the case where the intensity ratio is determined to be more than or equal to the set threshold, the detection device 100 turns off the power for detecting a pulse wave in the same manner as in Step S104 (S118). Then, the detection device 100 repeats the processing from Step S108.

Further, in Step S114, in the case where the intensity ratio is not determined to be more than or equal to the set threshold, the detection device 100 stands by for a set second standby time period (note that the following is satisfied: second standby time period<first standby time period) (S116). Then, the detection device 100 repeats the processing from Step S112.

Here, the second standby time period according to the present embodiment is, for example, several milliseconds to several tens of milliseconds. The second standby time period may be a fixed period that has been set in advance, or may be a variable period that can be changed in accordance with manipulation performed by a user or the like of the detection device 100.

By repeating the processing of Steps S112, S114, and S116, the detection device 100 can achieve "successive pulse wave detection of approximately 10 to 1000 times per second in the state in which the detection device 100 is mounted", for example.

Performing the processing shown in FIG. 5, for example, in the case where it is determined that the detection device 100 is mounted, the detection device 100 can detect a pulse wave. Further, performing the processing shown in FIG. 5, for example, in the case where it is not determined that the detection device 100 is mounted, the detection device 100 does not detect a pulse wave, and the power supply to the circuits for detecting the pulse wave is interrupted.

Accordingly, the detection device 100 can reduce the power consumption for detecting a pulse wave by performing the processing shown in FIG. 5, for example.

Note that the processing of the control method according to the present embodiment performed by the detection device 100 is not limited to the example shown in FIG. 5.

For example, in Step S112 of FIG. 5, in order to avoid detection of unexpected external light in the light receiving elements due to vibration of the detection device 100 and false detection of a pulse wave due to inclusion of noise in the signals output from the light receiving elements, the detection device 100 may measure intensity of several pulses of light. Further, in the case where the intensity of several pulses of light is measured in Step S112, and, in the case where it is determined in Step S114 of FIG. 5 that the intensity ratio is more than or equal to a set threshold for the set number of times successively, the detection device 100 determines that the detection device 100 is in the state of not being mounted.

Performing the processing according to the above-mentioned modified example, the detection device 100 can reduce influence of the unexpected external light and influence of the noise, and can enhance the effects achieved by performing the processing of the control method according to the present embodiment.

[II] Control Device According to the Present Embodiment

The device capable of being applied to the control method according to the present embodiment is not limited to the detection device shown in FIG. 3. As described above, the processing of the control method according to the present embodiment may be performed by the control device according to the present embodiment.

For example, the detection device to be controlled by the control device according to the present embodiment is the control device according to the present embodiment, the control device according to the present embodiment includes the same configuration as the detection device 100 shown in FIG. 3 (also includes the configuration according to the modified example).

Further, in the case where the detection device to be controlled by the control device according to the present embodiment is an external detection device, the control device according to the present embodiment is achieved as a device having the same function as the control unit 106 according to FIG. 3, for example. In the case of the above, the control device according to the present embodiment includes one or more processors including an arithmetic circuit such as MPU, and various processing circuits, and the processing of the control method according to the present embodiment is performed by the processors and the processing circuits.

To be more specific, the control device according to the present embodiment acquires, from an external detection device having the same configuration as shown in FIG. 3, data indicating a plurality of detection values, via any wired communication or radio communication through a communication device included in the control device or an external communication device connected to the control device.

Then, the control device according to the present embodiment performs the above processing (1) (Determination processing) on the basis of the data indicated by the acquired plurality of detection values, and determines the mounted state of the external detection device.

Further, the control device according to the present embodiment performs, for example, the above processing (2) (Control processing) on the basis of a determination result of the mounted state of the external detection device in the above processing (1) (Determination processing), and controls the operation related to detection of a pulse wave performed by the external detection device. The control device according to the present embodiment controls the operation related to detection of a pulse wave performed by the external detection device by, for example, transmitting a control signal corresponding to the determination result of the mounted state. The transmission of the control signal may be performed via any wired communication or radio communication through a communication device included in the control device or an external communication device connected to the control device, for example.

Note that the configuration of the control device according to the present embodiment is not limited to the example described above. For example, the control device according to the present embodiment may have a configuration corresponding to an example of application of the control device to be described later, for example.

[III] Examples of Effects Achieved by Using Control Method According to the Present Embodiment The detection device according to the present embodiment or the control device according to the present embodiment performs the processing of the control method according to the present embodiment, and accordingly the following effects are achieved, for example. Note that it is needless to say that effects achieved by performing the control method according to the present embodiment are not limited to the following effects.

- In a detection device configured to detect a pulse wave using PPG, a light emission frequency of a light source is switched automatically in accordance with a determination result of the mounted state of the detection device. Accordingly, the convenience of the user of the detection device can be enhanced.
- The mounted state of the detection device can be determined without providing the detection device with a sensor for detecting contact of a living body with the detection device, such as an infrared sensor. Accordingly, the cost of the detection device can be reduced.
- The mounted state of the detection device can be determined without providing the detection device with a sensor for detecting contact of a living body with the detection device, such as an infrared sensor. Accordingly, the size of the detection device can be reduced more easily.
- The mounted state of the detection device can be determined, as shown in FIG. 5, for example, only by emitting one pulse of light every standby time period (corresponding to the first standby time period) which is longer than the standby time period (corresponding to the second standby time period) for successive pulse wave detection. Accordingly, the power consumption in the detection device can be kept extremely low.
- Since it is not determined that the detection device is in the mounted state with a foreign substance such as external light or water, decrease in the convenience caused by false detection of the mounted state of the detection device and occurrence of useless power consumption due to the false detection can be prevented.

Heretofore, the detection device is given as an example of the present embodiment, but the present embodiment is not limited to such an embodiment. The present embodiment can be applied to various devices that can perform the processing of the control method according to the present embodiment and can have a function of detecting a pulse wave using PPG, such as "any wearable device that is used by being worn on the body of a user such as an eyewear device, a watch device, or a bracelet type device", "a computer such as a personal computer (PC)", "a communication device such as a smartphone", "a tablet device", "an imaging device such as a digital video camera or a digital still camera", "a game console", and "a mobile device such as a vehicle".

Further, the control device is given as an example of the present embodiment, but the present embodiment is not limited to such an embodiment. The present embodiment can be applied to various devices that can perform the processing of the control method according to the present embodiment, such as "any wearable device that is used by being worn on the body of a user such as an eyewear device, a watch device, or a bracelet type device", "a computer such as a PC", "a communication device such as a smartphone", "a tablet device", "an imaging device such as a digital video camera or a digital still camera", "a game console", and "a mobile device such as a vehicle". Further, the present embodiment can also be applied to a processing integrated circuit (IC) capable of being installed in the above devices, for example.

Program According to the Present Embodiment

A program (for example, a program capable of causing a computer to execute the processing of the control method according to the present embodiment, such as the above processing (1) (Determination processing) and the above processing (2) (Control processing)) for causing a computer to function as the detection device according to the present embodiment or the control device according to the present embodiment is executed by a processor or the like in the computer, and thus, the power consumption for detecting a pulse wave can be reduced.

Further, the program for causing a computer to function as the detection device according to the present embodiment or the control device according to the present embodiment is executed by a processor or the like in the computer, and thus, the effects achieved by the processing of the control method according to the present embodiment can be achieved.

It should be understood by those skilled in the art that various modifications, combinations, sub-combinations and alterations may occur depending on design requirements and other factors insofar as they are within the scope of the appended claims or the equivalents thereof.

For example, although it has been described in the above that there is provided the program (computer program) for causing a computer to function as the detection device according to the present embodiment or the control device according to the present embodiment, the present embodiment can also provide therewith a recording medium having the program stored therein.

The configuration described above shows an example of the present embodiment, and of course belongs to the scope of the technology according to the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1) A control device including:
a determination unit configured to determine a mounted state of a detection device on the basis of a plurality of detection values, the detection unit including a light source and a plurality of light receiving elements and detecting a pulse wave, the plurality of detection values corresponding to signals output in response to light beams received from the plurality of light receiving elements, respectively, distances between the light source and the respective plurality of light receiving elements being different from each other; and an operation control unit configured to control an operation related to detection of the pulse wave performed by the detection device on the basis of a determination result of the mounted state.

(2) The control device according to (1), in which
the operation control unit controls light emission of the light source included in the detection device on the basis of the determination result of the mounted state.

(3) The control device according to (2), in which
the operation control unit changes a light emission frequency of the light source based on whether the determined mounted state is a state in which the detection device is mounted or the determined mounted state is a state in which the detection device is not mounted.

(4) The control device according to any one of (1) to (3), in which
the operation control unit controls power supply to a circuit for detecting the pulse wave included in the detection device, on the basis of the determination result of the mounted state.

(5) The control device according to (4), in which
the circuit for detecting the pulse wave includes a circuit for acquiring the detection values.

(6) The control device according to (5), in which
the circuit for acquiring the detection values includes a light emission control circuit configured to control light emission of the light source.

(7) The control device according to (5) or (6), in which
the circuit for acquiring the detection values includes a measurement circuit configured to calculate the detection values using the signals output from the respective plurality of light receiving elements.

(8) The control device according to any one of (5) to (7), in which
the circuit for acquiring the detection values includes an amplification circuit configured to amplify the signals output from the respective plurality of light receiving elements.

(9) The control device according to any one of (4) to (8), in which
the circuit for detecting the pulse wave includes a pulse wave detection circuit configured to detect a pulse wave on the basis of the plurality of detection values.

(10) The control device according to any one of (1) to (9), in which
the determination unit
calculates a determination value for determining the mounted state on the basis of the plurality of detection values corresponding to two or more of the light receiving elements, respectively, distances between the light source and the respective light receiving elements being different from each other, and
determines the mounted state by comparing the calculated determination value to a predetermined threshold.

(11) A detection device including:
a light emission unit including a light source;
a light reception unit including a plurality of light receiving elements whose distances from the light source are different from each other;
a pulse wave detection unit configured to detect a pulse wave on the basis of a plurality of detection values corresponding to signals output in response to light beams received from the plurality of light receiving elements, respectively;

a determination unit configured to determine a mounted state on the basis of the plurality of detection values; and
an operation control unit configured to control an operation related to detection of the pulse wave on the basis of a determination result of the mounted state.

(12) A control method executed by a control device, the control method including:
determining a mounted state of a detection device on the basis of a plurality of detection values, the detection unit including a light source and a plurality of light receiving elements and detecting a pulse wave, the plurality of detection values corresponding to signals output in response to light beams received from the plurality of light receiving elements, respectively, distances between the light source and the respective plurality of light receiving elements being different from each other; and
controlling an operation related to detection of the pulse wave performed by the detection device on the basis of a determination result of the mounted state.

What is claimed is:
1. A control device comprising:
a determination unit configured to determine a mounted state of a detection device on the basis of a plurality of detection values, the detection unit including a light source and a plurality of light receiving elements and detecting a pulse wave, the plurality of detection values corresponding to signals output in response to light beams received from the plurality of light receiving elements, respectively, distances between the light source and the respective plurality of light receiving elements being different from each other; and
an operation control unit configured to control an operation related to detection of the pulse wave performed by the detection device on the basis of a determination result of the mounted state.

2. The control device according to claim 1, wherein
the operation control unit controls light emission of the light source included in the detection device on the basis of the determination result of the mounted state.

3. The control device according to claim 2, wherein
the operation control unit changes a light emission frequency of the light source on the basis of the determination result of the mounted state.

4. The control device according to claim 1, wherein
the operation control unit controls power supply to a circuit for detecting the pulse wave included in the detection device, on the basis of the determination result of the mounted state.

5. The control device according to claim 4, wherein
the circuit for detecting the pulse wave includes a circuit for acquiring the detection values.

6. The control device according to claim 5, wherein
the circuit for acquiring the detection values includes a light emission control circuit configured to control light emission of the light source.

7. The control device according to claim 5, wherein
the circuit for acquiring the detection values includes a measurement circuit configured to calculate the detection values using the signals output from the respective plurality of light receiving elements.

8. The control device according to claim 5, wherein
the circuit for acquiring the detection values includes an amplification circuit configured to amplify the signals output from the respective plurality of light receiving elements.

9. The control device according to claim 4, wherein
the circuit for detecting the pulse wave includes a pulse wave detection circuit configured to detect a pulse wave on the basis of the plurality of detection values.

10. The control device according to claim 1, wherein the determination unit
- calculates a determination value for determining the mounted state on the basis of the plurality of detection values corresponding to two or more of the light receiving elements, respectively, distances between the light source and the respective light receiving elements being different from each other, and
- determines the mounted state by comparing the calculated determination value to a predetermined threshold.

11. A detection device comprising:
a light emission unit including a light source;
a light reception unit including a plurality of light receiving elements whose distances from the light source are different from each other;
a pulse wave detection unit configured to detect a pulse wave on the basis of a plurality of detection values corresponding to signals output in response to light beams received from the plurality of light receiving elements, respectively;
a determination unit configured to determine a mounted state on the basis of the plurality of detection values; and
an operation control unit configured to control an operation related to detection of the pulse wave on the basis of a determination result of the mounted state.

12. A control method executed by a control device, the control method comprising:
determining a mounted state of a detection device on the basis of a plurality of detection values, the detection unit including a light source and a plurality of light receiving elements and detecting a pulse wave, the plurality of detection values corresponding to signals output in response to light beams received from the plurality of light receiving elements, respectively, distances between the light source and the respective plurality of light receiving elements being different from each other; and
controlling an operation related to detection of the pulse wave performed by the detection device on the basis of a determination result of the mounted state.

* * * * *